United States Patent [19]

Kiso et al.

[11] Patent Number: 4,534,206

[45] Date of Patent: Aug. 13, 1985

[54] STRIKE DIAGNOSIS APPARATUS

[75] Inventors: Mataichiro Kiso; Akemi Futakawa; Tokio Fukunaga, all of Hyogo, Japan

[73] Assignee: Mitsubishi Denki Kabushiki Kaisha, Japan

[21] Appl. No.: 451,201

[22] PCT Filed: Apr. 20, 1982

[86] PCT No.: PCT/JP82/00133

§ 371 Date: Dec. 7, 1982

§ 102(e) Date: Dec. 7, 1982

[87] PCT Pub. No.: WO82/03686

PCT Pub. Date: Oct. 28, 1982

[30] Foreign Application Priority Data

Apr. 20, 1981 [JP] Japan ................................. 56-60743
Feb. 13, 1982 [JP] Japan ................................. 57-23102

[51] Int. Cl.³ .............................................. G01N 3/30
[52] U.S. Cl. ............................................. 73/12; 73/82
[58] Field of Search ...................... 73/12, 78, 79, 82

[56] References Cited

U.S. PATENT DOCUMENTS

| 3,421,364 | 1/1969 | Moneypenny et al. ................. 73/82 |
| 3,502,983 | 3/1970 | Ingle et al. |
| 3,550,434 | 12/1970 | Schroeer et al. |
| 3,744,299 | 7/1973 | Bliss ................................... 73/12 X |
| 3,759,085 | 9/1973 | Wilson et al. |
| 4,157,655 | 6/1979 | Campbell et al. |

Primary Examiner—Charles A. Ruehl
Attorney, Agent, or Firm—Sughrue, Mion, Zinn, Macpeak & Seas

[57] ABSTRACT

The present invention relates to an insulation diagnosis technique for the coil of a generator or the like, especially a strike diagnosis apparatus for diagnosing the good or bad condition of insulation by comparing, directly or after a suitable processing signal, the magnitude of a strike signal applied to the generator's coil with a reference level, or by making a frequency analysis of the strike signal.

12 Claims, 17 Drawing Figures

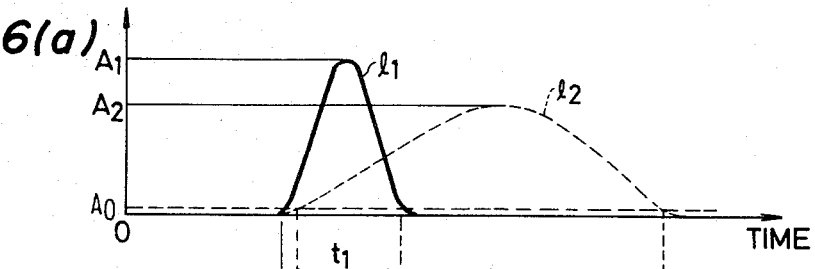
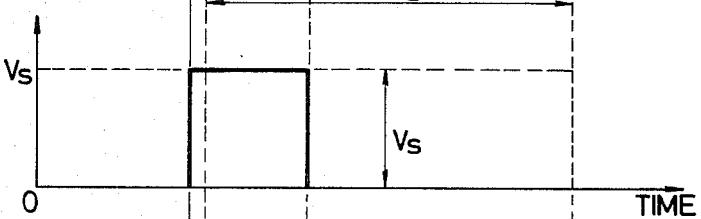
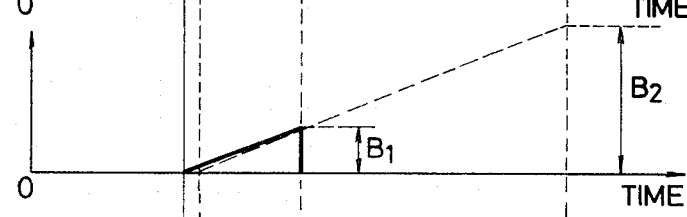
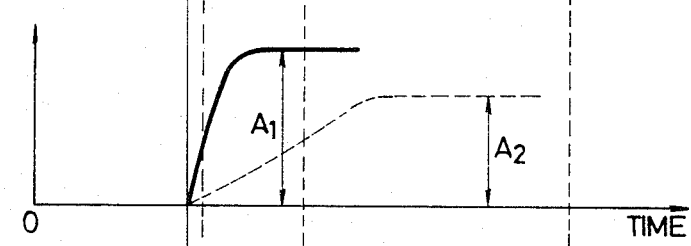
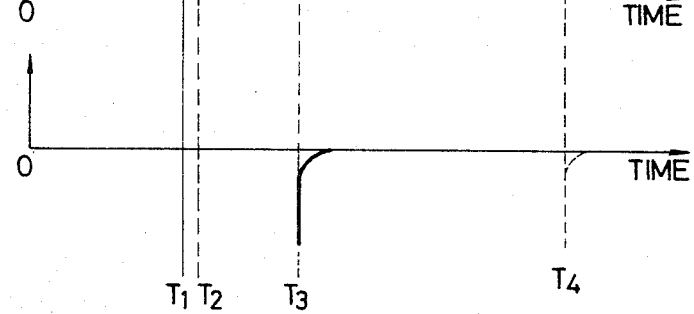

4,534,206

STRIKE DIAGNOSIS APPARATUS

FIELD OF THE ART

The present invention relates to a strike diagnosis apparatus for diagnosing insulation of coils or the like of a rotary machine such as a generator and an electric motor, in which only signal waveforms due to a striking force applied to the coil of the rotary machine are processed with respect to a time axis or a frequency axis thereby increasing an efficiency for the insulation diagnosis of the rotary machine's coil or the like.

BACKGROUND OF THE ART

FIG. 1 shows a conventional insulation testing method for a coil of a generator. In FIG. 1 a coil (1) is inserted into a slot (2A) of a core (2). As is apparent from FIG. 2 showing the schematic sectional view of the coil, the coil (1) is composed of a core wire (3) and an insulating member (4) surrounding the core wire (3). In the case where the coil (1) is used for a generator, the insulating member (4) is, in general, fixedly and closely contacted to the core wire (3). Therefore when the coil (1) is applied with striking force by a hammer (5), the coil (1) produces a striked sound "kon, kon" or "karn, karn" in accordance with the amount of the sectional area and the length of the core (1). A tester, using experience and perception obtained on the job, hears the strike sound and estimates the condition of the insulation of the insulating member (4) at each portion thereof.

It is well-known that even an insulating member (4), of the coil (1) which was initially estimated as a good condition is gradually deteriorated in insulation efficiency over years of use. The insulation efficiency of the insulating member (4) is deteriorated because the insulating member (4) covering the core wire (3) is swelled or peeled off.

In this case, upon the application of the striking force to the insulating member (4) by the hammer (5), the insulating member (4) produces a more dull sound such as "boko, boko" than the previously mentioned sounds indicative of good condition.

The tester has estimated hitherto the strike sounds produced for good conditions and inferior conditions by his sense of hearing. However, it is difficult and sometimes misleading to estimate the strike sound at a power-plant or a factory, at which the ambient noise is great. Further if a large striking force is applied to the insulating member (4) by the hammer (5) for the purpose of avoiding the misjudgement of the estimation, the insulation efficiency of the insulating member (4) becomes undesirably deteriorated even when the insulating member (4) is in a good condition. Therefore it is necessary to restrict the amount of strike force due to the hammer (5). Further the standards of estimation for the good or bad conditions is undesirably changed in accordance with the physical condition of the tester during the testing time over the course of a day.

DISCLOSURE OF THE INVENTION

The object of the present invention is to present a strike diagnosis apparatus capable of diagnosing a good or bad condition of an object to be striked on the basis of a detected striking force.

According to the present invention the good or bad condition of the object to be striked is judged or estimated by a peak value holding circuit for holding a signal representing the above striking force (hereinafter referred to as a strike signal), means for detecting the width of the strike signal on the axis of time, and dividing means for obtaining a ratio of the peak value and the width of the strike signal.

Further according to the present invention the good or bad condition of the object is judged by means of comparing the level of the strike signal with a reference level, further the condition is judged by analyzing the frequency of the strike signal and detecting a reduction amount of the level of a high region with respect to the level of a low region of the strike signal.

BRIEF DESCRIPTION OF THE DRAWINGS

FIGS. 6(a), 6(b), 6(c), 6(d), and 6(e) show output waveforms of a strike waveform or an amplifier, a Schmitt circuit, an integrator, a peak value holding circuit, and a negative pulse generating circuit respectively, in order;

THE BEST MODE FOR REALIZING THE PRESENT INVENTION

Figure 1:
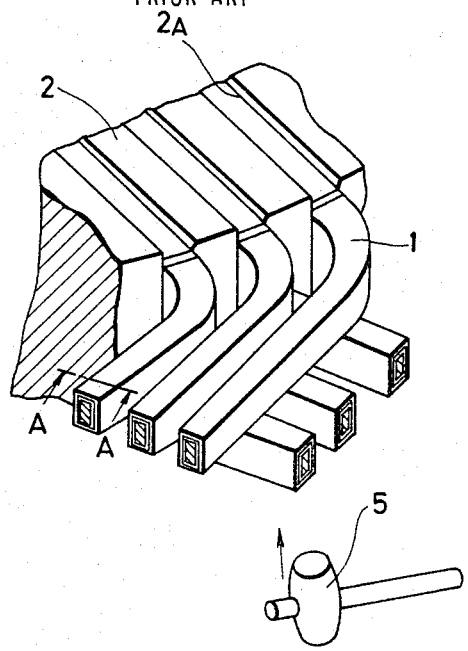
FIG. 1 is a perspective view showing a conventional method of testing a good or bad condition in insulation, in which coils of a generator are shown.
Figure 3:
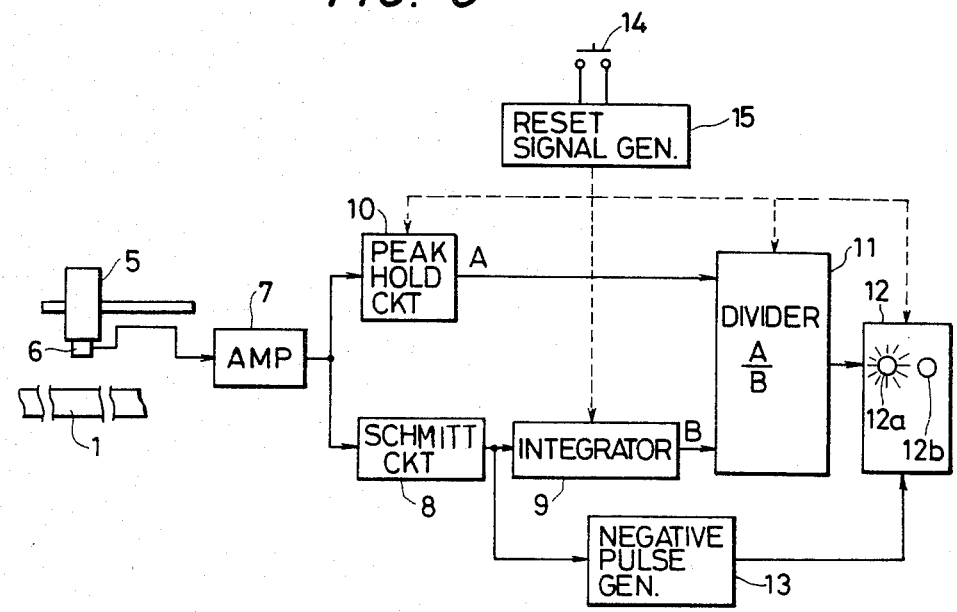
FIG. 3, FIG. 4 and FIG. 5 are block diagrams showing respective embodiments of the present invention, FIG. 4 being a block diagram showing a divider in FIG. 3, and FIG. 5 being a block diagram showing a judging device in FIG. 3.
Figure 4:
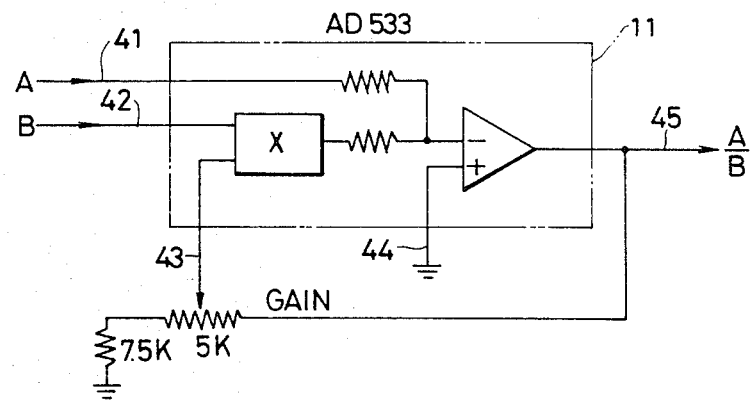
Figure 5:
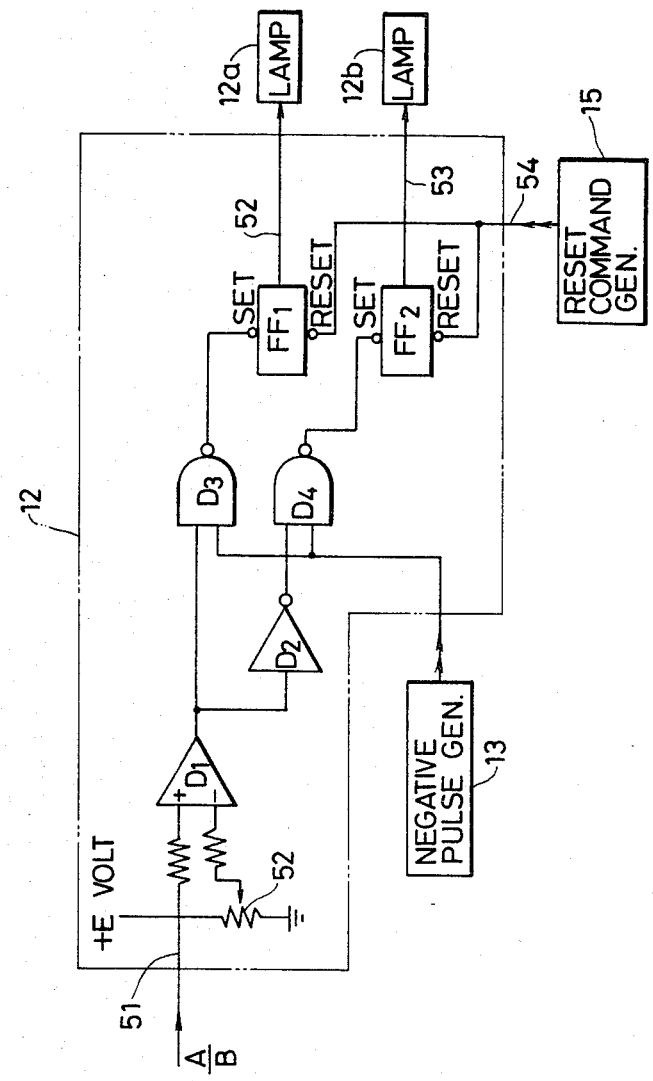

Referring now to FIGS. 3, 4 and 5 showing the best mode of the present invention, its construction and operation will be explained hereinafter. In FIG. 3 the same reference numeral is used for the same construction as that in FIG. 1. In FIG. 3 a pressure-sensitive element (6) is fixedly mounted on the strike surface of a hammer (5). An amplifier (7) is connected to the pressure-sensitive element (6) for amplifying the output of the pressure-sensitive element (6). A Schmitt circuit (8) is connected to the amplifier (7) to output an output voltage only when the magnitude of the output signal exceeds a predetermined level.

An integrator (9) is connected to the output of the Schmitt circuit (8) to integrate the output signal of the Schmitt circuit (8). A conventional integrator (9).

The peak value holding circuit (10) is connected to the amplifier (7) as well as the Schmitt circuit (8) to continuously hold the maximum value of the output signal of the amplifier (7) and output the signal representing the maximum value.

The divider (11) is connected to the integrator (9) and the peak value holding circuit (10) and has a function for dividing the output signals from them.

A specific construction of the divider (11) is as shown in FIG. 4, using the module AD 533 by ANALOG DEVICES COMPANY IN U.S.A. In FIG. 4 numerals (41) and (42) denote input leads for receiving the output signal A of the peak value holding circuit (10) and the output signal B of the integrator (9). Numeral (43) denotes an input lead for regulating the gain of the divider (11), numeral (44) an earth ground, and numeral (45) an output lead for outputting the value A/B.

Figure 2:
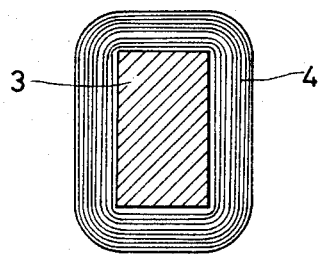
FIG. 2 is a sectional view taken along the line A—A in FIG. 1 showing the coils of the generator.

The judging device (12) is connected to the divider (11) for judging the good or bad condition of the insulation of the generator's coil, as shown in FIG. 2, by comparing the magnitude of the output signal of the divider (11) with the reference value. There are provided a lamp (12a) for indicating the good condition of the insulation and a lamp (12b) for indicating the bad condition. The lamps (12a) and (12b) may be composed of, for example, light emitting diodes.

Referring to FIG. 5 a specific construction of the judging device (12) is shown. In FIG. 5 numeral (51) denotes an input lead for receiving the output signal representing the value A/B of the divider (11), and $D_1$ denotes a comparator connected to a input lead (51) and a variable resistor (52) for generating a reference voltage corresponding to the reference value. A voltage +E volt is applied to the variable resistor (52). The module VA-741CE by Texas Instrument Corporation may be used for the comparator ($D_1$). ($D_2$) denotes an inverter for inverting the output of the comparator ($D_1$) which may be provided by module SN7404 manufactured by the Texas Instrument Corporation. ($D_3$) denotes a NAND circuit for receiving the output signal of the comparator ($D_1$) and the negative pulse generating circuit (13), and ($D_4$) denotes a NAND circuit for receiving the output signal of the negative pulse generating circuit (13) and the output of the inverter ($D_2$). Both of the NAND circuits may be provided by module SN7400 manufactured by the Texas Instrument Corporation.

($FF_1$) denotes a flip-flop set by the output signal of the NAND circuit ($D_3$) to generate a driving signal for driving the lamp (12a), and the flip-flop ($FF_1$) usually outputs a signal maintained at a low level by the output signal of a reset signal generating circuit (15).

($FF_2$) denotes a flip-flop set by the output signal of the NAND circuit ($D_4$) to generate a driving signal for driving the lamp (12b). Both of the flip-flops ($FF_1$) and ($FF_2$) may be provided by module SN7474 manufactured by the Texas Instrument Corporation.

The operation of the judging device (12) is as follows.

In the case where the value A/B is larger than the reference value, only the lamp (12a) is energized. The operation for energizing the lamp (12a) will be explained hereinafter.

When the value A/B is larger than the reference voltage received at the negative terminal of the comparator ($D_1$), the output of the comparator ($D_1$) becomes positive (+). Then a negative pulse from the negative pulse generating circuit (13) is received into the judging device (12), the output of the NAND circuit ($D_3$) becomes a high level (H). When a voltage of high level is applied to the SET terminal of the flip-flop ($FF_1$) beforehand reset by a reset command generator, the flip-flop ($FF_1$) is inverted to energize the lamp (12a) composed of the light emitting diode.

Further, when the value A/B is larger than the reference value, the output signal (+) of the comparator ($D_1$) is inverted by the inverter ($D_2$), then the negative signal (−) is inputted into the NAND circuit ($D_4$). Therefore the output of the NAND circuit ($D_4$) does not become the high level (H) even when the negative pulse is applied to the other input terminal of the NAND circuit ($D_4$) thereby not to reverse the flip-flop ($FF_2$).

On the other hand, when the value A/B is smaller than the reference value only the lamp (12b) is energized. The operation of the energization is as follows. In case of the value A/B less than the reference voltage the output of the comparator ($D_1$) is maintained in negative voltage. Therefore the output of the NAND circuit ($D_3$) does not become the high level for energizing the lamp (12a) even when the negative pulse is applied to the NAND circuit ($D_3$). Further, when the output of the comparator ($D_1$) is the negative voltage the output of the inverter ($D_2$) becomes positive (+). Accordingly in the case where the negative pulse signal is applied to the NAND circuit ($D_4$) the output of the NAND circuit ($D_4$) becomes the high level to reverse the flip-flop ($FF_2$) from the reset state to the set state thereby energizing the lamp (12b).

Further the judging device (12) receives the output signal of the Schmitt circuit (8) through the negative pulse generating circuit (13). A push switch (14) is connected to the reset command generator (15) to actuate the reset command generator (15) when the push switch (14) is closed. The command signal of the reset command generator (15) is applied to the integrator (9), the peak value holding circuit (10), the divider (11) and the judging device (12) to reset the operation of them.

Figure 7:
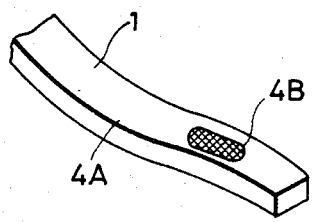
FIG. 7 is a perspective view of the generator's coil having an insulating portion.

Referring now to the operation of the strike diagnosis apparatus, an application example of the generator's coil (1) will be explained with reference to FIG. 7. Numerals (4A) and (4B) denote a good insulation portion and a defective insulation portion respectively. In the case where the good insulation portion (4A) and the defective insulation portion of the generator's coil (1) are struck by the hammer (5), the reaction striking force given to the hammer (5) differs respectively, in accordance with the differing hardness of the coil's surfaces. Therefore the pressure-sensitive element (6) mounted on the hammer (5) for converting the striking force to an electric signal produces different output signals, as shown by the solid line and the dotted line of FIG. 6(a). The solid and dotted lines show signals from the good and defective insulation portions, respectively. In the case of a hard surface being struck, that is the good insulation portion (4A), the output signal of the pressure-sensitive element (6) usually has a waveform having a large crest value and a small width, as shown by the solid line. On the other hand, in the case of a soft surface being struck, that is the defective insulation portion (4B), the output signal of the pressure-sensitive element (6) usually has a waveform having a small crest value and large width, as shown by the dotted line. The output signals of the pressure-sensitive element (6) are amplified by the amplifier (7), so that the output signal of the amplifier (7) takes on a similar wave-form, only with a larger magnitude. The output signal of the amplifier (7) is applied to the Schmitt circuit (8) and the peak value holding circuit (10). The Schmitt circuit (8) produces the output voltage Vs only when the magnitude of the input signal exceeds the value Ao in FIG. 6(a). First, a signal corresponding to the good insulation portion (4A) and secondly, a signal corresponding to the defective insulation portion (4B) will be explained hereinafter. Upon application of the solid-line waveform having the maximum value $A_1$ to the Schmitt circuit (8), the voltage at the point $T_1$ of time is Ao as shown in FIG. 6(a), so that the output voltage of the Schmitt circuit (8) becomes Vs as shown in FIG. 6(b). The output voltage Vs of the Schmitt circuit (8) is maintained for the period $t_1$, i.e. the period from the point $T_1$ of time to the point $T_3$ of time at which the input voltage is less than Ao. Upon application of the output voltage Vs of the Schmitt circuit (8) to the integrator (9), the integrator (9) starts the integrating operation at the point $T_1$ of time and stops the integrating operation at the point $T_3$ of time thereby to produce the output voltage $B_1$. The output voltage $B_1$ is applied to the divisor side of the divider (11). On the other hand, the output signal of the amplifier (7) is also applied to the peak value holding circuit (10), and the output voltage of the peak value holding circuit (10) is continuously maintained in the maximum voltage $A_1$ as shown by the solid line in FIG. 6(d). The maximum voltage $A_1$ is applied to the dividend side of the divider (11). Then the divider (11) outputs the output voltage proportional to the ratio $A_1/B_1$ or $A_1/t_1$ to input it to the judging device (12).

Secondly, the operation of the Schmitt circuit (8) and the peak value holding circuit (10) with respect to the signal corresponding to the defective insulation portion (4B) will now be explained. Upon application of the signal as shown by the dotted line, having the maximum value $A_2$, in FIG. 6(a) to the Schmitt circuit (8), the voltage exceeds the value Ao at the period from the point $T_2$ of time to the point $T_4$ of time, so that the output voltage Vs of the Schmitt circuit (8) becomes Vs for the period $t_2$. When the output voltage $V_s$ is applied to the integrator (9), the integrator (9) produces the output voltage the final value of which is $B_2$, as shown by the dotted line in FIG. 6(c). The final value $B_2$ is applied to the divisor side of the divider (11). On the other hand, the peak value holding circuit (10) usually holds the maximum voltage $A_2$, as shown by the dotted line of FIG. 6(d), so that the maximum voltage $A_2$ is applied to the dividend side of the divider (11). Then the divider (11) produces the output voltage proportional to the ratio $A_2/B_2$ or $A_2/t_2$ to input it to the judging device (12).

The negative pulse generating circuit (13) is composed to produce a negative pulse at the point $T_3$ or $T_4$ of time, i.e. the instant that the output signal of the Schmitt circuit (8) goes to zero from the voltage Vs as shown in FIG. 6(e). After the judging device (12) receives the negative pulse and the output voltage applied from the divider (11) is compared with a reference voltage which is arbitrarily set in the judging device (12), the status of the insulation is determined. As a result of the comparison the lamp (12a) for indicating the good condition of insulation is energized when the output voltage of the divider (11) is larger than the reference voltage, on the other hand, when the output voltage of the divider (11) is smaller than the reference voltage the lamp (12b) is energized to indicate the defective condition of insulation.

In case of judging the condition of the insulating member (4) by the judging device (12), it is preferable for obtaining a clear judgement to compare the ratio $A_1/t_1$ with the ratio $A_2/t_2$, rather than merely to compare the maximum value $A_1$ with the maximum value $A_2$. In FIG. 6(a), if, for example, $A_1:A_2=3:2$ and $t_1:t_2=1:3$, in case of the comparison of the maximum values of the input waveform, the ratio $A_1/A_2$ becomes 1.5, in contrast with the other comparison of $A_1/t_1/A_2/t_2=4.5$. Further in the comparison of the maximum value of the input waveform it becomes difficult to judge the good insulation portion (4A) and the defective insulation portion (4B) due to the input waveform, because of deviations of the striking force of the hammer (5) for striking the coil (1). However, according to the embodiment of the present invention, the maximum amplitude is divided by the time width, so that a variation in the striking force due to the hammer (5) will not affect the correctness of the output of the judging circuit.

As stated above, according to the embodiment of the present invention a clear difference with respect to the good insulation portion (4A) and the defective insulation portion (4B) can be obtained in comparison with the comparison method of the maximum values of the input waveform.

Thus the first judgement is terminated, and then if the tester pushes the push switch (14) to conduct judgement again a reset command signal is produced from the reset command generator (15) to apply it to the integrator (9), the peak value holding circuit (10), the divider (11) and the judging device (12) thereby to return the initial state thereof for starting the judging operation.

Figure 8:
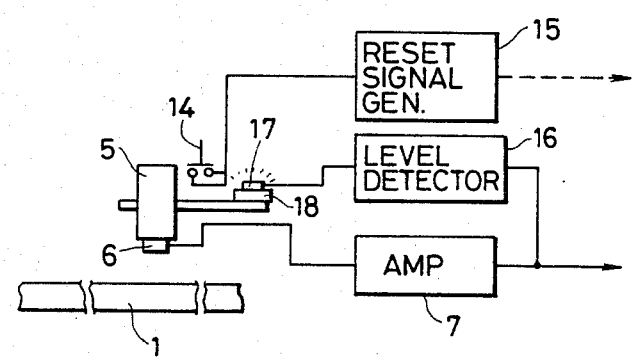
FIG. 8 is a block diagram showing a portion of another embodiment of the present invention.

FIG. 8 shows a block diagram indicating a portion of another embodiment of the strike diagnosis apparatus of the present invention. In FIG. 8, a level detector (16) produces the output thereof when the output of the amplifier (7) is saturated.

There is provided an overload lamp (17) mounted to the hammer (5) through a cushion (18) and energized by the output of the level detector (16). In the embodiment of FIG. 8, the push switch (14) is provided on or in adjacent to the hammer (5), in contrast with the embodiment of FIG. 3 in which the push switch (14) is provided at the remote portion from the hammer (5) of the strike diagnosis apparatus. Therefore, according to the embodiment of FIG. 8, the push switch (14) can be closed each strike operation of the hammer (5) to effect smoothly a cyclic operation of strike, judgement and reset by means of the construction that the push switch (14) is provided on the handle or in adjacent to the hammer (5), in contrast with the embodiment of FIG. 3 in which the tester must go to the strike diagnosis apparatus, providing the push switch (14), to push the push switch (14), often each judgement. In the embodiment of FIG. 8, there is provided a delay circuit within the reset signal generating circuit (15) for outputting the reset signal after judgement of the good or bad condition of the insulating member (4) is terminated.

The embodiment of FIG. 8 does not consider a saturation of the output signal from the amplifier (7). In the saturation of the output signal from the amplifier (7), the reliability of the judgement results is surely deteriorated. Then according to the embodiment of FIG. 8, the level detector (16) is connected to the output side of the amplifier (7), and the over load lamp (17) energized by the output of the level detector (16) is mounted on the handle of the hammer (5) through the cushion (18), further the level detector (16) is composed to output a constant output voltage when the output of the amplifier (7) is saturated. Therefore, if the striking force due to the hammer (5) is excessive, the over load lamp (17) is energized to indicate the excessive striking force by the hammer (5). In this case the saturation of the amplifier (7) can be avoided by making small the striking force of the hammer (5) or by reducing the amplifying ratio of the amplifier (7).

In the above-mentioned embodiments the indication of the judgement is made by the lamps (12a) and (12b), but alternatively it may be made by a meter or a number to obtain similar effects. Further the insulating member (4) of the coil (1) is diagnosed in the above-mentioned embodiments, however, the object to be diagnosed is not limited to the coil (1), and the present application can also be used to determine the hardness of an object.

With respect to the above-mentioned embodiments, an apparatus for diagnosing the good or bad condition of an object by striking the object will be explained hereinafter.

Figure 9:
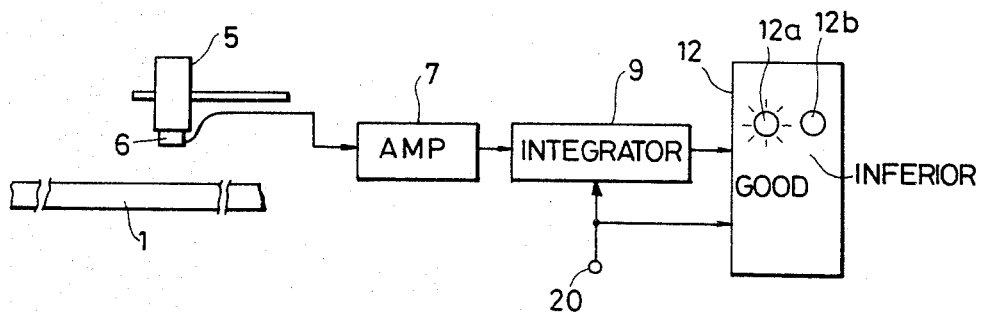
FIG. 9, FIG. 10, FIG. 11 and FIG. 12 are block diagrams showing other embodiments of the present invention.

FIG. 9 is a block diagram showing a strike diagnosis apparatus with the most simple circuit construction. The same reference numerals are given to the same or equivalent parts as that of FIG. 3. Numeral 20 denotes a terminal for receiving the reset signal. In the construction as shown in FIG. 9, upon application of the striking force due to the hammer (5) to the generator's coil (1), the striking force is detected by the pressure-sensitive element (6) and amplified by the amplifier (7). The strike signal representing the striking force, which is amplified by the amplifier (7) is the same as that shown in FIG. 6(a). The integrator (9) operates to integrate the strike signal for a predetermined period to obtain an integration value. The integration value has an interrelationship with the good or bad condition of insulating of the generator's coil (1), and the good or bad condition of the generator's coil (1) can be judged by the integration value by means of comparing the integration value with a reference value. The indication of the judged results is the same as that in FIG. 3.

Figure 10:
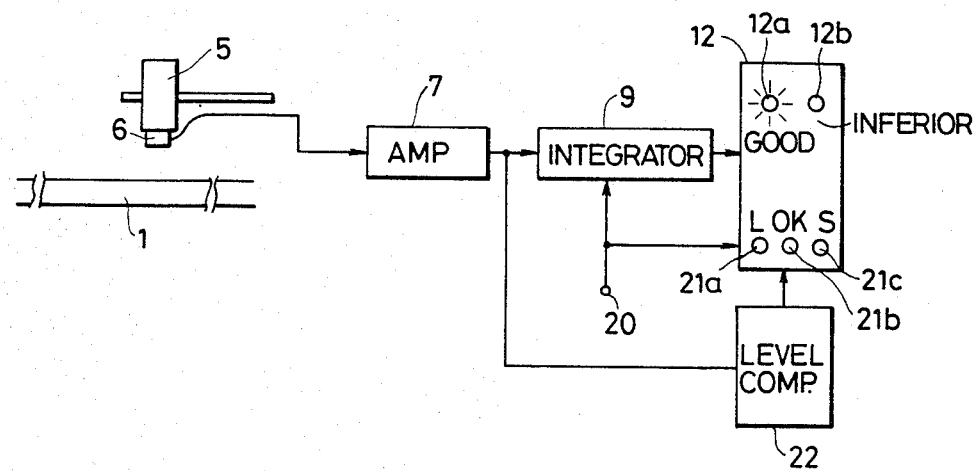

FIG. 10 shows another embodiment of the present invention in which a level of the striking force is judged by comparing the magnitude of the striking force with a reference value by a level comparator (22), to indicate as to whether the striking force is large, good (OK), or small, so that the judging device (12) can make a suitable diagnosis of a good (OK) condition of the striking force. Thus the embodiment of FIG. 10 has an advantage for avoiding a poor diagnosis due to a large or small striking force.

Figure 11:
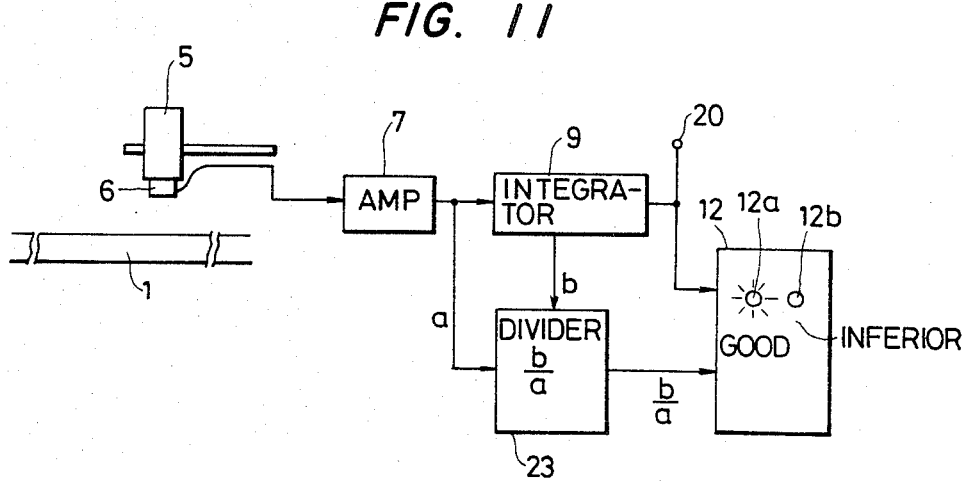

Referring now to FIG. 11 another embodiment of the present invention for avoiding a poor diagnosis due to a large or small striking force will be explained hereinafter. In FIG. 11, the output a of the amplifier (7) is divided by the output b of the integrator (9) by means of a divider (23), to obtain the divided output b/a. The output b/a is compared with a predetermined reference voltage set in the judging device (12) to judge the good or bad condition of the insulating member (4). According to the strike diagnosis apparatus shown in FIG. 11, even when the striking force is large the diagnosis of the insulating member (4) can usually be achieved by applying the reset signal to the reset input terminal (20) each strike operation, regardless to the magnitude of the striking force, because the output b of the integrator (9) representing the integrated value of the strike waveform is divided by the output a of the amplifier (7) representing the value proportional to the striking force.

Figure 12:
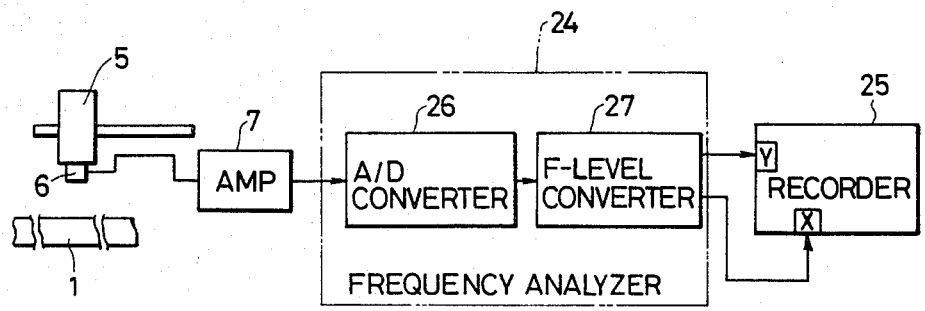

Referring now to FIG. 12 another embodiment of the present invention using a method of frequency analysis different from the above-mentioned embodiments will be explained hereinafter.

FIG. 12 shows another embodiment of the present invention, relating to a method of diagnosing an insulating member covering a conductor. An electromechanical converting element such as the pressure-sensitive element (6) is mounted on the striking surface of the hammer (5). The amplifier (7) is connected to the pressure-sensitive element (6) to amplify the output signal from the pressure-sensitive element (6). A frequency analyzer (24) is provided for the purpose of the frequency analysis of the output signal from the amplifier (7), and the analysis result is displayed and recorded by a recorder (25). The frequency analyzer (24) is composed of an A/D converter (26) for converting the analog signal to the digital signal and a frequency level converter (27). Upon application of the strike to the generator's coil (1) by the hammer (5), the strike signal as shown in FIG. 6(a) is detected by the pressure-sensitive element (6), as stated in the above descriptions. In FIG. 6(a) the letters $l_1$ and $l_2$ show the signals corresponding to the good insulation portion (4A) and the defective insulation portion (4B) respectively. In the case where the surface of the coil (1) to be striked is hard, that is the good insulation portion (4A), the output signal from the pressure-sensitive element (6) has usually a waveform having a large crest value and small width as shown by the solid line ($l_1$) in FIG. 6(a). On the other hand, in case of a soft surface to be applied with the strike, that is the defective insulation portion (4B), the output signal of the pressure-sensitive element (6) has usually a waveform having a small crest value and large width as shown by the dotted line ($l_2$) in FIG. 6(a). The output signal of the pressure-sensitive element (6) is amplified by the amplifier (7), so that the output signal of the amplifier (7) becomes a signal with a large amplitude, similar to the input signal of the amplifier (7) as shown in FIG. 6(a).

Figure 13:
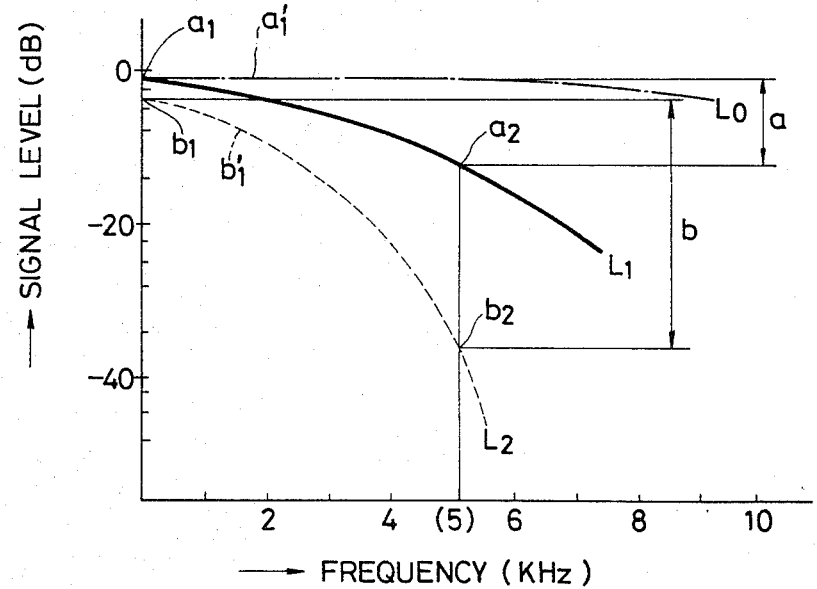
FIG. 13 shows a characteristic representing frequency analysis data for explaining the operation of the embodiment in FIG. 12.

FIG. 13 shows an example of frequency analysis data recorded in the recorder (25). The ordinate denotes decibels (dB) of the signal level along a logarithmic axis. The solid line $L_1$ and the dotted line $L_2$ in FIG. 13 show the frequency analysis data of signals due to the striking operation at the good insulation portion and the defective insulation portion respectively. (See the lines $l_1$ and $l_2$ of FIG. 6(a))

As shown by the data the waveform $l_1$ with a small width has a high region component in comparison with the waveform $l_2$ with a large width. The strike signal detected in case of striking the extremely hard portion such as iron, has a flat frequency characteristic parallel to the abscissa as shown by the letter Lo in FIG. 13 in which the signal level in the lower region is similar to that in the higher region of frequency. As shown by such data, the signal corresponding to the good insulation portion has a large level in the higher region because of the hard surface of the coil (1), on the other hand the signal corresponding to the defective insulation portion has a small level in the lower region because of the soft surface of the coil (1).

A a judgement of the good or bad condition of the object to be judged on the basis of the above data characteristic, will be explained hereinafter. The frequency 5 KHz in FIG. 13 is one suitably set for check by the tester in consideration of the level reduction in the high region, and the set frequency may be changed suitably in accordance with the pattern of the obtained data. The point $a_1$, is a contact point of the curve $L_1$, the point $a_2$ the value in the curve $L_1$ at 5 KHz, the value a (dB) is the difference between the points $a_1$ and $a_2$, $b_1$ is a contact point of the curve $L_2$, the point $b_2$ the value in the curve $L_2$ at 5 KHz, and the value b (dB) is the difference between the points $b_1$ and $b_2$. In FIG. 13 the points $a_1$ and $b_1$ are not coincident with each other because there is a difference in the magnitude of strike signal. In case of obtaining, the characteristic of the curve $L_2$, if the striking force is increased, both of the points $b_1$ and $b_2$ are also increased. However, because of the ordinate in logarithmic scale, the difference b dB between the points $b_1$ and $b_2$ is not changed. Therefore it is not necessary for the points $a_1$ and $b_1$ to be the same value when comparing the differences a and b.

The inventors of the present invention, as a result of many experiments on the coil, confirmed that the amount a (dB) of level reduction at 5 KHz with respect to a good insulation condition is smaller than the amount b (dB) of level reduction at 5 KHz with respect to a defective insulation condition. Further it was also confirmed that the coil with a small level reduction has a high dielectric breakdown voltage, and the coil with a large level reduction has a low dielectric breakdown voltage.

Thus, the diagnosis of the good or bad condition of insulation is easily achieved in such a manner that the striking force is applied to a coil, the condition of the coil insulation not yet known, and by using the strike diagnosis apparatus as shown in FIG. 12 and the data as shown in FIG. 13, the magnitude of the level reduction (corresponding to the differences a and b in FIG. 13) at the check frequency (for example, 5 KHz) is detected in order to judge the good or bad condition of insulation.

The insulation may be diagnosed by using an automatic apparatus for automatically obtaining the amount of the level reduction a and b. Further in case of obtaining the amounts of the level reduction a and b, it may be also effective to obtain the amount of the respective level reduction by comparing the point $a_1'$ with the point $a_2$ and the point $b_1'$ with the point $b_2$ the points $a_1'$ and $b_1'$ as, being reference value of the lower frequency region as shown in FIG. 13, in place of obtaining the amount of level reduction by comparing the point $a_1$ with the point $a_2$ or the point $b_1$ with the point $b_2$.

As mentioned above according to the embodiment of the present invention, a precise testing can be achieved regardless of the ambient noise and the physical condition of the tester, in such a manner that the striking signal detected by the electromechanical converting element mounted on the striking body is analyzed in frequency and the amount of the level reduction is obtained to diagnose the good or bad condition of the object to be tested.

The present invention can be utilized for an insulation test of a generator's coil, an electric motor's coil and the like.

We claim:

1. A strike diagnosis apparatus comprising means for detecting a striking force produced by a strike applied to an object to be striked and for generating a strike signal representing said striking force, and means for judging the good or bad condition of said object on the basis of the strike signal, wherein said judging means is composed of a peak value holding circuit for holding a peak value of said strike signal, signal width detecting means for detecting a signal width of said strike signal in the axis of time, and a divider for obtaining the ratio of said peak value and said signal width.

2. A strike diagnosis apparatus according to claim 1, wherein said signal width detecting means is composed of a Schmitt circuit for producing an output signal when the output of said peak value holding circuit exceeds a predetermined level, and an integrator for integrating the output of said Schmitt circuit, and the contents of said peak value holding circuit, said Schmitt circuit, said integrator and said divider being reset by a reset signal.

3. A strike diagnosis apparatus as claimed in claim 2 further comprising a hammer for applying said striking force to said object to be striked, and wherein said detecting and generating means comprises a pressure sensitive element fixedly mounted relative to the strike surface of said hammer to provide an electrical output signal corresponding to said striking force.

4. A strike diagnosis apparatus as claimed in claim 3 further comprising a reset signal generator and a manually actuable switch for actuating said reset signal generator to generate said reset signal.

5. A strike diagnosis apparatus according to claim 1, further comprising an amplifier for amplifying said strike signal and a display device for displaying the saturation state of the output of said amplifier.

6. A strike diagnosis apparatus according to claim 5, wherein said display device is composed of a level detector for detecting the level of the output of said amplifier to produce the output thereof when the detected level exceeds a predetermined value, and an overload lamp for being energized by the output of said level detector.

7. A strike diagnosis apparatus as claimed in claim 6 further comprising a hammer for applying said striking force to said object to be striked, and wherein said detecting and generating means comprises a pressure sensitive element fixedly mounted relative to the strike surface of said hammer to provide an electrical output signal corresponding to said striking force.

8. A strike diagnosis apparatus according to claim 7, wherein said signal width detecting means is composed of a Schmitt circuit for producing an output signal when the output of said peak value holding circuit exceeds a predetermined level, and an integrator for integrating the output of said Schmitt circuit, and the contents of said peak value holding circuit, said Schmitt circuit, said integrator and said divider being reset by a reset signal.

9. A strike diagnosis apparatus as claimed in claim 8 further comprising a reset signal generator and a manually actuable switch for actuating said reset signal generator to generate said reset signal.

10. A strike diagnosis apparatus as claimed in claim 9 wherein said manually actuable switch means is positioned on said hammer.

11. A strike diagnosis apparatus as claimed in claim 10 wherein said overload lamp is placed on said hammer.

12. A strike diagnosis apparatus as claimed in claim 6 further comprising a hammer for applying a striking force to said object to be striked, and wherein said overload lamp is placed on said hammer.

* * * * *